United States Patent [19]
Nokihara et al.

[11] Patent Number: 5,395,594
[45] Date of Patent: Mar. 7, 1995

[54] SIMULTANEOUS MULTIPLE CHEMICAL SYNTHESIZER

[75] Inventors: Kiyoshi Nokihara, Uji; Makoto Hazama, Kyoto; Rintaro Yamamoto, Kyoto; Shin Nakamura, Kyoto, all of Japan

[73] Assignee: Shimadzu Corporation, Kyoto, Japan

[21] Appl. No.: 933,729

[22] Filed: Aug. 24, 1992

[30] Foreign Application Priority Data

Aug. 26, 1991 [JP] Japan .................. 3-240553

[51] Int. Cl.$^6$ .............................................. B01J 8/02
[52] U.S. Cl. .................. 422/135; 73/863.22; 73/864.22; 73/864.23; 73/864.24; 73/864.25; 422/100; 422/101; 422/130; 422/131; 422/231; 935/88
[58] Field of Search ............ 422/130, 131, 135, 63, 422/100, 101, 231, 261; 935/88; 73/864.22, 864.24, 864.25, 863.23, 863.32

[56] References Cited

U.S. PATENT DOCUMENTS

| | | | |
|---|---|---|---|
| 3,536,449 | 10/1970 | Astle | 422/63 X |
| 3,715,190 | 2/1973 | Won Kil Park et al. | 935/88 X |
| 3,842,680 | 10/1974 | Vollick et al. | 73/864.22 |
| 4,106,911 | 8/1978 | Marcelli | 422/63 |
| 4,543,238 | 9/1985 | Mimura et al. | 422/63 |
| 4,895,706 | 1/1990 | Root et al. | 422/101 X |
| 4,920,056 | 4/1990 | Dasgupta | 422/130 X |
| 4,974,458 | 12/1990 | Koike | 73/864.25 |

FOREIGN PATENT DOCUMENTS

| | | |
|---|---|---|
| 0355582 | 2/1990 | European Pat. Off. . |
| 8808872 | 12/1988 | Germany . |
| 4005518 | 2/1990 | Germany . |
| 9113084 | 9/1991 | WIPO . |

OTHER PUBLICATIONS

G. Schnorrenberg et al., Tetrahedron, vol. 45, No. 24, 1989, Oxford GB, pp. 7759-7764.
Bruce Merrifield, Solid Phase Synthesis, Science vol. 232, pp. 341-347 (1986).

*Primary Examiner*—Robert J. Warden
*Assistant Examiner*—Amalia L. Santiago
*Attorney, Agent, or Firm*—Birch, Stewart, Kolasch & Birch

[57] ABSTRACT

The present invention is directed to a simultaneous multiple chemical synthesizer comprising a number of reaction vessels wherein each vessel has a filter in the bottom portion thereof, a number of needles wherein each needle is connected to an aspiration injection line of a reaction mixture and a gas supply line in connection with each reaction vessel and each needle does not touch the resin contained in the reaction vessel, a number of arms which are horizontally and vertically movable and hold the respective needles, a bubbling gas line and a waste discharge line in connection with each reaction vessel, wherein each line is connected to the bottom portion of each reaction vessel, a number of purging means which move synchronously with said waste discharge lines, and means for washing the portions of the needles and purge means which contact with the reaction reagents.

6 Claims, 5 Drawing Sheets

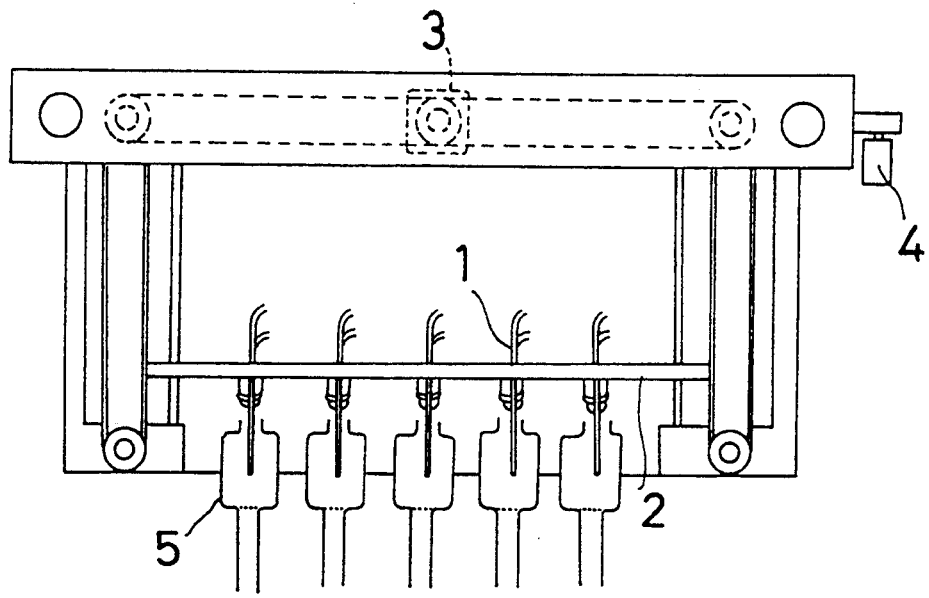
F I G. 1
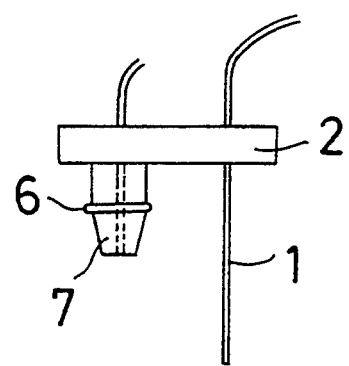
F I G. 2

SIMULTANEOUS MULTIPLE CHEMICAL SYNTHESIZER

FIELD OF THE INVENTION

The present invention relates to a simultaneous multiple chemical synthesizer.

BACKGROUND OF THE INVENTION

In conventional solid-phase synthesizers, particularly multiple synthesizers wherein a single needle is used for all of a number of reaction vessels, repeated reaction tends to cause incomplete reaction, cross contamination, increased frequency in moving of the needle, and the like. This problem arises due to the different reactivities of individual chemical derivatives in the case of multiple reactions. In addition, from the viewpoint of efficiency-related factors, such as yield and purity of reaction product, it is disadvantageous to carry out all reactions by the same method or under the same conditions. Moreover, the single needle must be frequently moved reciprocally among a large number of reaction vessels, various reagent containers and washing ports, which results in increased operating time or side reactions. Specifically, when a single needle is used with a number of reaction vessels, while the needle is acting on one reaction vessel, the other reaction vessels must wait, and in addition, washing must be completed by the reach of the needle to another reaction vessel, which results in an increase in time required for each reaction. This method is also disadvantageous from the viewpoint of the mechanical strength and durability of the apparatus, because it involves a large number of movements. Moreover, when a needle contacts with resin by bubbling or stirring in the reaction vessel, the resin attaches to the needle, thereby causing loss of resin and cross contamination.

In the apparatus wherein the reagents in respective reaction vessels are aspirated and discharged on a one-by-one basis by a needle, not only the discharge of the reagents, washing solvents, etc. is incomplete, but also thorough washing is essential for each discharge, which results in cross contamination.

In the apparatus wherein the reagents are simultaneously discharged from all reaction vessels under reduced pressure with the bottom portion thereof kept at a negative pressure, there are some difficult problems in the maintenance of tightness between the vessels and the bottom portion containers and in uniform discharge due to the differences in the properties of reaction products among the items.

Also, in conventional methods, it must be outside the reaction apparatus to take out the reaction product from the solid phase by another deprotecting reaction, namely cleavage, after reaction, i.e., they are not efficient solid-phase synthesizing methods.

SUMMARY OF THE INVENTION

It is an object of the present invention to provide a simultaneous multiple chemical synthesizer which allows simultaneous multiple chemical reactions with high efficiency in terms of reaction yield, purity of synthesized product, rapidness, low cost, easy maintenance, etc.

In view of the problems described above, the present inventors have made investigations and have found that it is possible to realize a high-efficiency production by using separate systems for respective reactions, thereby solving problems such as the reduction of reaction efficiency in conventional reaction apparatus.

Accordingly, the present invention is directed to a simultaneous multiple chemical synthesizer, each reaction lane being arranged independently, comprising a number of reaction vessels wherein each vessel has a filter in the bottom portion thereof, a number of needles wherein each needle is connected to an aspiration injection line of a reaction mixture and to a gas supply line for each reaction vessel, a number of arms which are horizontally and vertically movable and hold the respective needles, a bubbling gas line and a waste discharge line for each reaction vessel, wherein each line is connected to the bottom portion of each reaction vessel, a number of purge portions which move synchronously with said waste discharge lines, and means for washing the portions of the needles and the purge portions which contact the reaction reagents.

BRIEF DESCRIPTION OF THE DRAWINGS

The present invention will become more fully understood from the detailed description given hereinbelow and the accompanying drawing which is given by way of illustration only, and thus, is not limitative of the present invention, and wherein:

FIG. 1 is a schematic diagram of the simultaneous multiple chemical synthesizer of the present invention;

FIG. 2 is a schematic diagram of needle and purge means in the simultaneous multiple chemical synthesizer of the present invention;

Figure 3:
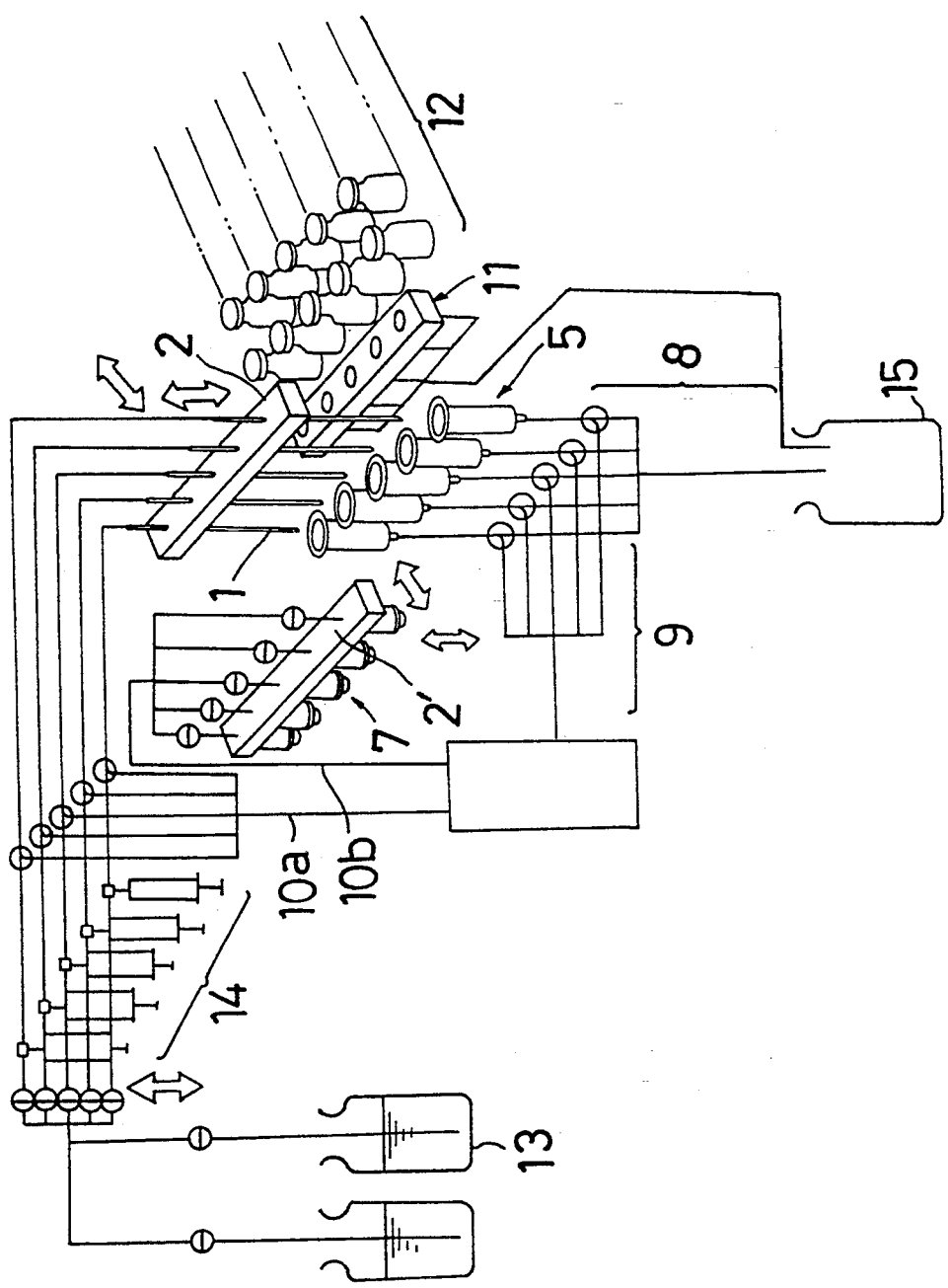
FIG. 3 is a schematic diagram of a solid-phase synthesizer with the simultaneous multiple needle of the present invention.

The reference numbers in FIGS. 1 through 6 denote the following elements:

Element 1 is a needle, element 2 an arm, element 2' an arm, element 3 a motor, element 4 a motor, element 5 a reaction vessel, element 6 an O ring, element 7 a purge nozzle, element 8 a waste discharge line, element 9 a gas line for bubbling, element 10a a gas supply line, element 10b a gas supply line, element 11a washing port, element 12 reactant station, element 13 a bottle for washing solvent, element 12 a microsyringe for aspiration and injection and element 15 a bottle for waste liquid.

DETAILED DESCRIPTION OF THE INVENTION

FIG. 1 is a schematic diagram of the simultaneous multiple chemical synthesizer of the present invention.

Motors 3 and 4 are provided so that arm 2, which holds needle 1 etc., can be moved horizontally and vertically, respectively. Needle 1 is connected with a series of aspiration injection line with microsyringe 14 for aspirating and injecting solvent or reagents, etc. from reactant station 12 to reaction vessel 5 and connected with gas supply line 10a for injecting the gas into reaction vessel 5. The purge portion is provided to seal the upper face of reaction vessel 5 and supply the unreacted reagents, solvents and washing solvents to waste discharge line 8 by a gas pressure exerted by gas introduction after completion of reaction or resin washing, and it is configured with purge nozzle 7, which is equipped with O-ring 6 for tight sealing. As illustrated in FIG. 2, needle 1, and purge nozzle 7, which is equipped with O-ring 6 for tight sealing, are fixed to arm 2; a number of pairs thereof each of which is in charge of each reaction vessel are equipped, as illustrated in FIG. 1.

In FIGS. 1 and 3, five reaction lanes are shown, but this number of lanes can be increased or decreased. Also, in FIGS. 1 and 2, needle 1 and purge nozzle 7 are attached to the same arm 2, but they may be attached to separate driving arms 2 and 2', as illustrated in FIG. 3.

Desirably, reaction vessel 5 is a disposable reaction vessel having a filter in the bottom portion thereof. As an example, a polypropylene reaction vessel packed with a polyalkylene filter in the bottom portion thereof may be mentioned. Examples of polyalkylene filter materials include polypropylene, polyethylene and polyvinylidene fluoride, with preference given to polypropylene. There is no limitation on the pore size of the filter or the thickness of the filter layer packed in the reaction vessel, as long as they are in the ordinary range; for example, the pore size of the filter is such that the resin, which is 200 to 400 mesh (63 to 125 $\mu$m) in size, cannot pass the filter, and it is usually about 5 to 10 $\mu$m.

Any material can be used for the main body of the reaction vessel, as long as it is not likely to generate static electricity on the solid-phase resin support; polypropylene is preferred, since it is cheap and shows little unspecific adsorption of the resulting peptide. Such a filter in the reaction-vessel need not be pre-treated before using the reaction vessel, because it is free of the problem of easy clogging. Therefore, polypropylene is suitable for simultaneous multiple chemical syntheses as in the present invention.

FIG. 3 is a schematic diagram of a solid-phase synthesizer based on the simultaneous multiple chemical synthesizer illustrated in FIG. 1. Reaction vessel 5 is a disposable reaction vessel having a filter in the bottom portion thereof, wherein a solid-phase resin support is packed, as described above; for each reaction vessel, a needle 1 and a purging means comprising purge nozzle 7 is driven. Any purge gas can be used, as long as it does not affect the reaction; for example, nitrogen gas, which is cheap, is preferred. The needles do not touch the resin support.

Bubbling gas lines 9 are for gas introduction to reaction vessel 5 via the bottom portion thereof for stirring the reaction mixture in order to accelerate and uniformize the reaction, while waste discharge lines 8 are for discharging wastes such as the unreacted reagents, solvents and by-products from reaction vessel 5 via the bottom portion thereof after completion of the reaction. Bubbling gas line 9 and waste discharge line 8 are connected to the bottom portion of reaction vessel 5 via a three-way valve or another means.

Also, gas supply line lob for discharging the reagents and solvents from the reaction vessel is connected to the above-mentioned purge nozzle 7, via which a gas is introduced to discharge the waste from the reaction vessel to bottle for waste 11quid 15. Bubbling gas lines 9 and waste discharge lines 8 exist for each reaction vessel 5.

Also, an aspiration injection line with microsyringe 14, which is for aspirating the reaction mixture of solvent, reagents, etc. from reactant station 12 and injecting them into the reaction vessel, also serves as a line for injecting the washing solvent from bottle for washing solvent 13 into the reaction vessel. The microsyringe is equipped with a syringe and a motor which independently drives a piston for each reaction vessel so that different volumes of reaction mixture can be supplied to the reaction vessel of each line. Gas supply line 10a is used to cause bubbling to thoroughly mix the starting material, reagents, solvents, catalysts, etc. set on reactant station 12 to prevent degradation after they are injected via aspiration injection line with microsyringe 14. Said aspiration injection line with microsyringe 14 and gas supply line 10a are connected to a needle through a line via a three-way valve.

As means for washing the portions of needle 1 and purge nozzle 7 at the purging means, which contact the reaction reagent, washing port 11 is provided, where said contact portions are washed after injection of the reagent and after completion of the reaction.

Reactant station 12, bottle for washing solvent 13, etc. permit optional selection of the number thereof according to the route of synthesis. They may also be automated by microprocessor control.

As an example of the use of the simultaneous multiple chemical synthesizer of the present invention, a peptide synthesis using BOP/HOBt is described below. First, a resin support containing reaction vessel 5 is set in position, and HOBt (N-hydroxybenzotriazole), NMM (N-methylmorpholine), piperidine, methanol, t-butyl methyl ether and each $N_\alpha$ protected amino acid (powder) together with PyBOP ® (benzotriazole-1-yloxy-tris-pyrrolidino-phosphonium hexafluorophosphite; produced by Novabiochem A.G) are placed on reactant station 12 corresponding to the reaction vessel. Bottle for washing solvent 13 contains DMF (dimethylformamide) as a washing of a reactant dissolving solvent. The following operations are controlled by a microprocessor.

1. DMF Wash

DMF is injected to reaction vessel 5 via an aspiration injection line; a gas is supplied via bubbling gas line 9 to wash the resin; the upper face of the reaction vessel is closed tight at the purge portion; the DMF in reaction vessel 5 is purged into bottle for waste liquid 15.

2. Piperidine Wash

Needle 1 is moved to the piperidine container in reactant station 12 by means of robot arm 2, and the piperidine is aspirated into an aspiration injection line, after which the needle is moved to reaction vessel 5, and the piperidine solution is injected, followed by bubbling in the same manner as DMF wash to deprotect the $N_\alpha$ protecting group of the first amino acid bound on the resin. After completion of the reaction, purging is performed.

3. Piperidine Wash

The same as piperidine wash step 2.

4. DMF Wash

The same as DMF wash step 1.

5. Amino acid activation

To the container which contains the amino acid together with PyBOP, BOP or TBTU (2-(1H-benzotriazole-1-yl)-1,1,3,3-tetramethyluronium tetrafluoroborate) to be next incorporated, which is set up on the reactant station, HOBt solution and NMM solution are injected by means of robot arm 2 and needle 1. After discharging the liquids from needle 1 and microsyringe 14 at washing port 11, the contents in the container containing the amino acid is dissolved by bubbling with the gas supplied from the needle tip.

6. Coupling Reaction

The amino acid activated in step 5 is transferred to reaction vessel 5 via an aspiration injection line with microsyringe 14 and bubbled via bubbling gas line 9; after completion of the reaction, purging is performed.

7. DMF Wash

The same as DMF wash step 1.

The above steps are repeated in a number of cycles equivalent to the number of amino acids to be synthesized. Then, after the above step 4 is completed as the final cycle, the resin is washed with methanol and t-butyl methyl ether in the same manner as for the piperidine treatment, and the resin is finally dried with the nitrogen gas introduced from the purging means.

The simultaneous multiple chemical synthesizer of the present invention is particularly suitable for the synthesis of biochemical substances such as peptides, nucleic acids and sugar chains. The apparatus of the present invention is characterized in that 1) time requirement per reaction can be shortened because the aspiration injection lines of reaction mixture are independently used for respective reaction vessels, because the waste discharge lines are also independent, and because each needle is in charge of each reaction vessel, 2) the problems of side reactions and cross contamination can be solved because means for washing the contact portions is provided, and 3) cleavage, namely a reaction for taking out the desired reaction product from the solid phase, can be carried out simultaneously in the apparatus of the present invention because the reaction vessels used have a particular filter. Also, individual reactions can be monitored because the waste discharge lines are independently arranged for respective reaction vessels.

The use of the apparatus of the present invention allows simultaneous multiple chemical reactions (e.g., solid-phase peptide synthesis) with high efficiency in terms of reaction yield, time required for synthesis, and synthesized product purity. Also, the ease of peptide synthesis varies widely depending on the type and sequence of the constituent amino acids of the desired peptide; the use of the apparatus of the present invention allows simultaneous multiple syntheses even when different reagents and different reaction methods are used for respective reaction systems. For these reasons, in synthesizing the same desired peptide by different methods, the apparatus of the present invention makes it possible to 1) evaluate the reagents for synthesis and 2) evaluate the methods for synthesis at the same time. Furthermore, because the apparatus of the present invention is capable of simultaneously synthesizing a several types of similar compounds and related compounds, its applicability is wide and it is useful in epitope mapping, structure-activity correlation studies and screening of more active analogues.

EXAMPLES

Example 1

Synthesis of the Opioid Peptide Leucine Enkephalin Comprising 5 Amino Acids

H-Tyr-Gly-Gly-Phe-Leu-OH was synthesized simultaneously in 8 reaction channels A through H, and the differences among the reaction channels were investigated.

Using Fmoc-Leu-p-benzyloxybenzyl alcohol resin (30 mg) as the solid support, $N_\alpha$-Fmoc amino acids activated with PyBOP®-HOBt were sequentially incorporated from the C-terminus in the presence of N-methylmorpholine (NMM). Before the introducing (coupling) reaction, the $N_\alpha$-Fmoc group was removed with 30% piperidine in DMF, followed by washing with DMF alone. Because the resin substitution rate was 0.38 meq/g, the reaction capacity of the 30 mg starting resin was 11.4 μmol. Thus, calculated yield of the desired product (molecular weight 555.62) is 6.33 mg, about 6.0 to 7 mg of cleaved peptide was obtained in each lane.

The synthesis schedule used in this reaction is shown below. The reaction apparatus, under microprocessor control, was automatically operated in this order of reaction steps for each component.

| [Calculation Table for Synthesis] | | | |
|---|---|---|---|
| Lane | A, B, C, D, E, F, G, H | | |
| Strategy | Fmoc/Mod.BOP-HOBT | | |
| Peptide | Leu—Enkephalin | | |
| Sequence | Tyr—Gly—Gly—Phe—Leu—OH | | |
| | $C_{28}H_{37}N_5O_7$ (mwt: 555.64) | | |
| Resin | Fmoc—Leu-p-benzyloxybenzyl alcohol resin | | |
| | Resin Substitution | 0.38 meq/g | |
| | Resin Quantity | 30.00 mg | |
| Free Peptide (theor. yield) | | 6.33 mg | |
| Amino Acid Station (Excess 10 fold) | | 114 μmol | |
| 4:Fmoc—Phe—OH | | mwt = 387.44 | 44.17 mg |
| 3:Fmoc—Gly—OH | | mwt = 297.31 | 33.89 mg |
| 2:Fmoc—Gly—OH | | mwt = 297.31 | 33.89 mg |
| 1:Fmoc—Tyr(tBu)—OH | | mwt = 459.54 | 52.39 mg |
| PyBOP | mwt: 520.3 (× 1.0 eq) | | 59.31 mg/Coupling |
| NMM | 110 ml/mol (× 1.5 eq) | | 171.0 μl/Coupling |
| | 1.0 mmol/ml in DMF | | |
| HOBt | mwt: 135.1 (× 1.0 eq) | | 228.0 μl/Coupling |
| | 0.5 mmol/ml in DMF | | |

| [Step] | [Operation] | [Times] |
|---|---|---|
| | [Synthesis Schedule] | |
| 1 | DMF Wash | 1 min. × 1 |
| 2 | Piperidine (30% in DMF) Wash | 5 min. × 1 |
| 3 | Piperidine (30% in DMF) Wash | 3 min. × 1 |
| 4 | DMF Wash | 1 min. × 5 |
| 5 | Activation of Amino Acids | 1 to 3 min. |
| 6 | Coupling (Mixing with Resin) | 30 min. |
| 7 | DMF Wash | 1 min. × 4 |
| | [Final Cycle] | |
| 100 | DMF Wash | 1 min. × 1 |
| 101 | Piperidine Wash | 5 min. × 1 |
| 102 | Piperidine Wash | 3 min. × 1 |
| 103 | DMF Wash | 1 min. × 5 |
| 104 | Methanol Wash | 1 min. × 2 |
| 105 | t-butylmethylether | 0.5 min. × 1 |
| 106 | Nitrogen Blow | 10 min. |

In this case, 3 bottles were prepared; piperidine (30 % in DMF), methanol and t-butylmethylether. On the reactant station, each amino acid was weighed with PyBOP® as shown in calculation table, Fmoc-Phe-OH, Fmoc-Gly-OH, Fmoc-Gly-OH, Fmoc-Tyr(tBu)-OH, NMM solution in DMF and HOBt solution in DMF were placed; the gas used was gaseous nitrogen. The reaction vessel used was of polypropylene, packed with a polypropylene filter therein.

After completion of the peptide chain elongation, the resulted protected peptide resin having the $N_\alpha$-Fmoc group was treated with 30 % piperidine in DMF and then was cleaved (the cleavage reaction being the simultaneously removal of side chain protecting groups with peptide chain removal from the support) with trifluoroacetic acid (TFA) containing 5% anisole and 1% ethanedithiol while remaining in the reaction vessel; the resulting mixture was precipitated with diethyl ether and centrifuged. The resulting precipitate was dissolved in 10% acetic acid and lyophilized to yield a crude pentapeptide. The following shows common procedures of cleavage after synthesis and of free peptide recovery. This reaction was performed in each reaction vessel used for the synthesizing reaction at the same time. Accordingly, Dry the reaction vessel under reduced pressure→
Remove the protective group (cleavage cocktail 0.3 to 0.5 ml/reaction vessel)→
Mix slowly→
Filter while blowing nitrogen gas from the upper portion of the reaction vessel→
Collect the filtrate (0.3 to 0.5 ml) in centrifugal tube→
Precipitate with cold diethyl ether (15 ml)→
Centrifuge (3000 rpm, 5 minutes)→
Decanted, wash with diethyl ether and centrifuge twice→
Dry with nitrogen gas stream for 1 to 2 minutes→
Dissolve in 30% acetic acid (0.5 ml)→
Dilute with water (2 to 3 ml)→
Lyophilize→
Obtain a crude peptide.

Figure 4:
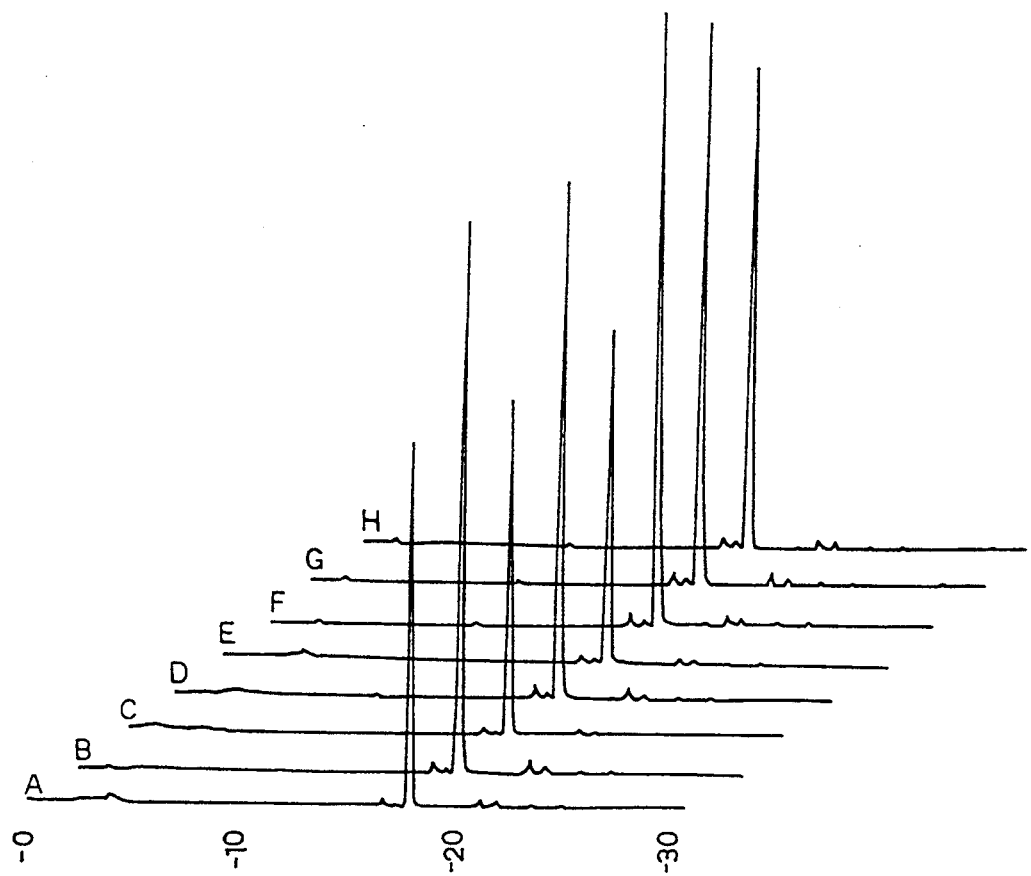
FIG. 4 is a chromatogram of crude cleaved leucine enkephaline in reversed-phase HPLC which was simultaneously and independently synthesized in 8 reaction channels in Example 1, using the apparatus of the present invention.

Yield was constant at 6.5±0.5 mg among the 8 channels. The results of reversed-phase HPLC are shown in FIG. 4. The analytical conditions for the reversed-phase HPLC were as follows.

Column: SynProPep* RPC18 (4.6×250 mm)
* =Trademark
Eluent: 0.01N HCl/CH$_3$CN=85/15 to 55/45 (30 min.)
Flow Rate: 1.0 ml/min. Absorbance: 210 nm There was no difference among channels A through H, and high purity was shown. The peptide obtained was identified as the desired product by sequence analysis and mass spectrometry.

Example 2

Synthesis by the Simultaneous Different Coupling Method

The tripeptide H-Gly-His-Lys-OH, a hepatocyte growth factor, was synthesized simultaneously by the following 4 coupling methods A through D. The starting resin used was Fmoc-Lys(Boc)-p-benzyloxybenzyl alcohol resin.

A: Method using DICD (diisopropylcarbodiimide), the acyl component converted to an active ester by means of HOBt was reacted with the amino component on the solid-phase resin support.

B: Method using PyBOP ® and HOBt (the same as in Example 1 described above).

C: Method using the uronium salt TBTU (2-(1H-benzotriazole-1-yl)-1,1,3,3-tetramethyluronium tetrafluoroborate) in place of PyBOP ®.

D: Method using PfP Ester (pentafluoro ester of amino acid).

Figure 5:
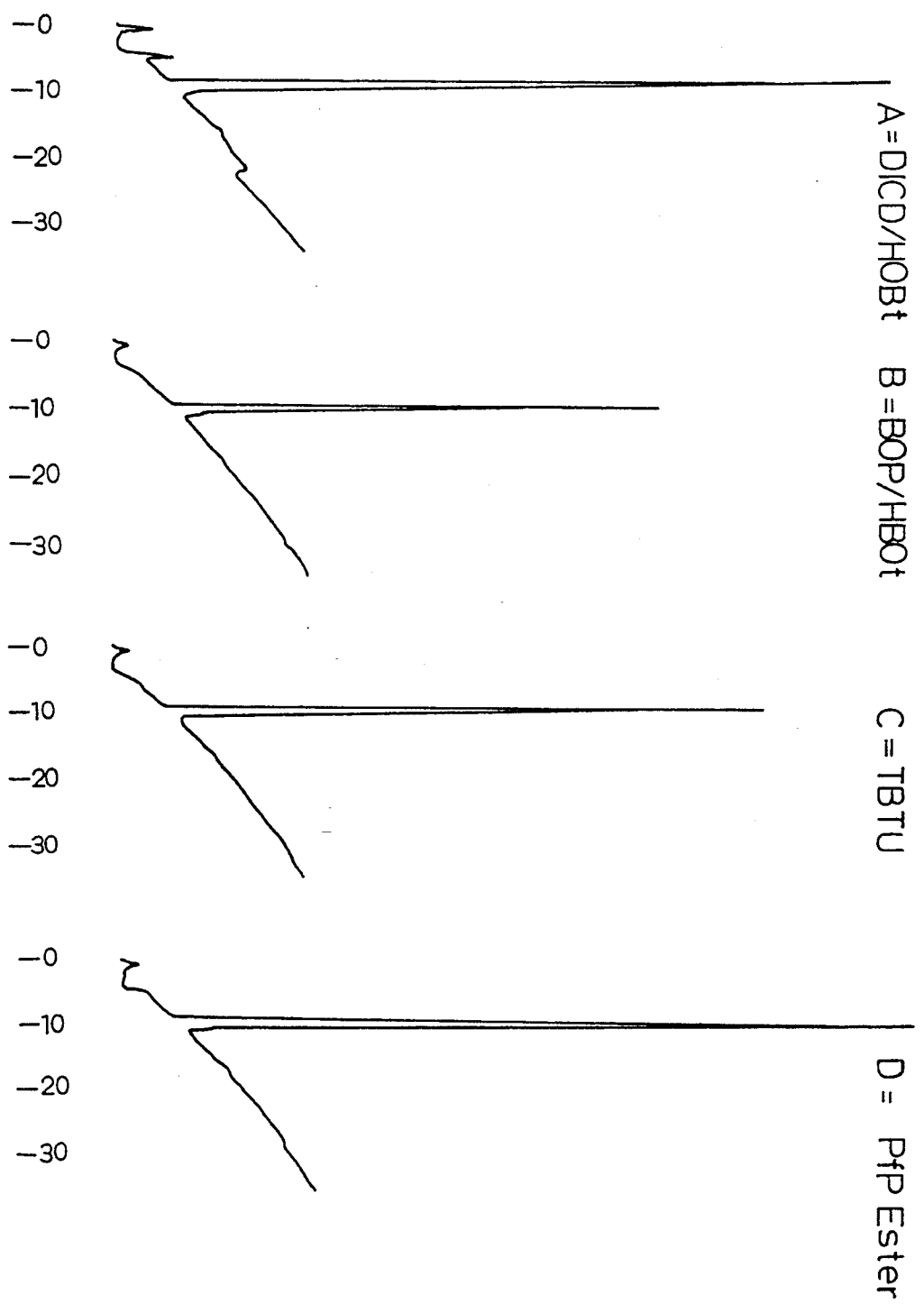
FIG. 5 is a chromatogram of HPLC of tripeptide synthesized in Example 2 using the apparatus of the present invention.
Figure 6:
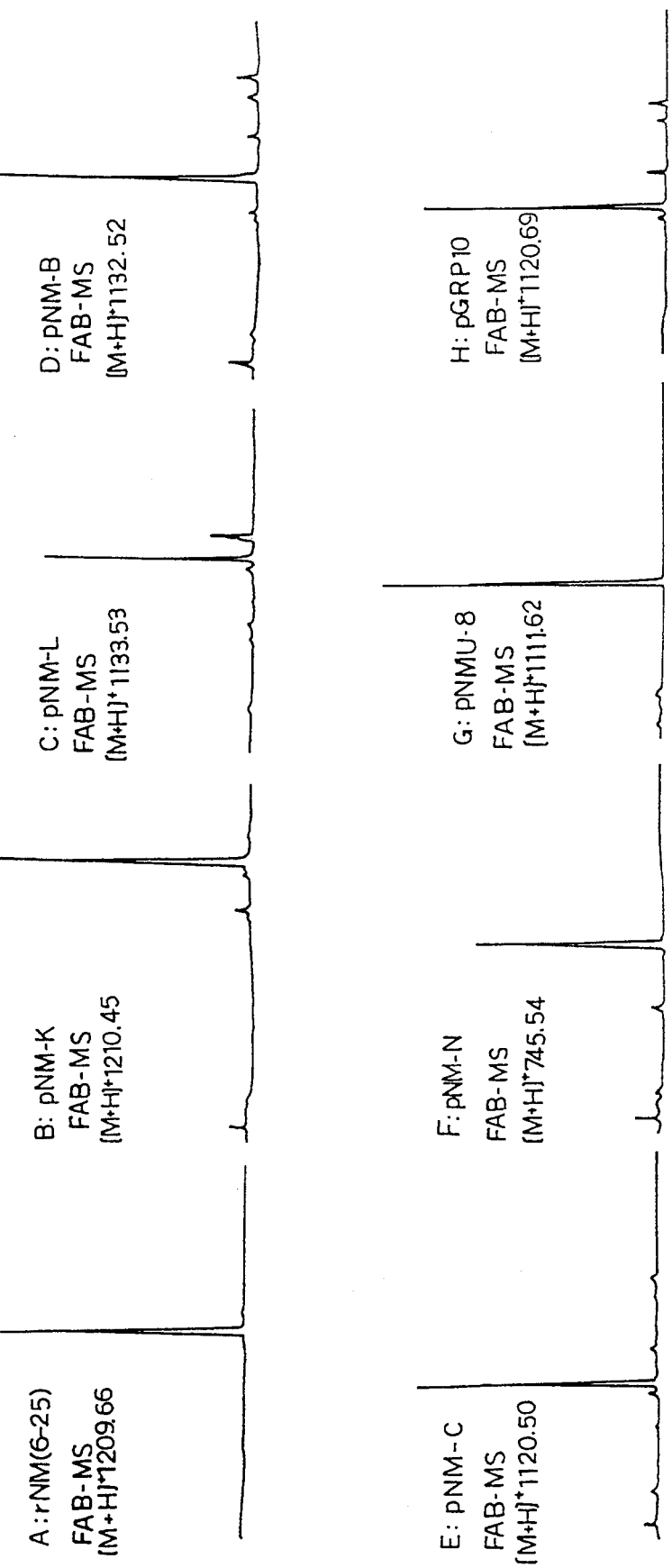
FIG. 6 is a chromatogram in reversed-phase HPLC of 8 different crude peptides obtained by simultaneous cleavage in Example 3 using the apparatus of the present invention.

In any case, synthesis was performed according to the schedule shown in Example 1, and cleavage was performed using the reaction vessel as such by the method described in Example 1. The HPLC pattern of tripeptide obtained are shown in FIG. 5. The analytical conditions for the reversed-phase HPLC were as follows.

Column: SynProPep* Pep Kat (4.0×50 mm)
* =Trademark
Eluent: 5 mM NaH$_2$ PO$_4$/5 mM NaH$_2$ PO$_4$+1M NaCl=100/0 to 75/25 (30 min.)
Flow Rate: 1.0 ml/min. Absorbance: 210 nm The resulting peptide also shows good efficiency and satisfied by sequence analysis, etc.

Example 3

Simultaneous Multiple Syntheses

Using 8 independent channels, peptides with respectively different amino acid sequences were simultaneously synthesized and cleaved to provide 8 crude desired peptides with yields close to the theoretically calculated values respectively. These syntheses were achieved in accordance with the schedule and cleavage procedure as described in Example 1.

In this synthesis, the cleavage cocktails used were: 94% TFA (trifluoroacetic acid), 5% anisole and 1% ethanediol (EDT)(90 min); 94% TFA, 3% anisole, 3% EDT and 5 mg of 2-methylindole (90 min) for Trp containing peptides; 82% TFA, 5% water, 5% thioanisole, 3% EDT 2% methylethylsulfide and 3% phenol (6 hrs) for Arg containing peptides.

The 8 different crude peptides (lanes A through H), the method for coupling the starting resin, and other data are shown below.

Fmoc Amino Acid: 10 fold excess against amino component
Coupling: PyBOP ®-HOBt-NMM (1:1:1.5)
The side chain protection groups used were:
Asp=OBut; Arg=Pmc; Asn, His=Trt; Ser, Thr, Tyr=tBu
Starting resin: PAL TM resin* (50 mg, the substitution group=0.21 mmol/g, 10.5 μmol)
*5-(4'-(9-Fluorenylmethyloxy-carbonyl)aminomethyl-3,5-dimethoxyphenoxy)-valeric acid handle attached to p-methylbenzhydryl-amine resin Lane A: Rat Neuromedin (16–25) (MW=1208.42)
   H-Gly-Gly-Phe-Phe-Leu-Phe-Arg-Pro-Arg-Asn-NH$_2$
Lane B: Porcine S.C.Neuromedin-K (MW=1209.22)
   H-Asp-Met-His-Asp-Phe-Phe-Val-Gly-Leu-Met-NH$_2$
Lane C: Porcine S.C.Neuromedin-L (MW=1132.34)
   H-His-Lys-Thr-Asp-Ser-Phe-Val-Gly-Leu-Met-NH$_2$
Lane D: Porcine S.C.Neuromedin-B (MW=1131.31)
   H-Gly-Asn-Leu-Trp-Ala-Thr-Gly-His-Phe-Met-NH$_2$
Lane E: Porcine S.C.Neuromedin-C (MW=1119.30)
   H-Gly-Asn-His-Trp-Ala-Val-Gly-His-Leu-Met-NH$_2$
Lane F: Porcine S.C.Neuromedin-N (MW=743.98)
   H-Lys-Ile-Pro-Tyr-Ile-Leu-NH$_2$
Lane G: Porcine S.C.Neuromedin-U8 (MW=1110.32)
   H-Tyr-Phe-Leu-Phe-Arg-Pro-Arg-Asn-NH$_2$
Lane H: Porcine S.C.GRP-10 (MW=1119.30)
   H-Gly-Asn-His-Trp-Ala-Val-Gly-His-Leu-Met-NH$_2$ For peptide synthesis on lane A, for instance, a 30% piperidine solution in DMF as an N$_\alpha$-deprotecting reagent, DMF, methanol, t-butyl methyl ether, etc. as bottle for washing solvents, and an NMM solution in DMF and an HOBt solution in DMF for the activation reaction were prepared. On the reactant station, mixtures of each of various protected amino acid derivatives together of PyBOP ® such as Fmoc-Gly-OH, Fmoc-Gly-OH, Fmoc-Phe-OH, Fmoc-Phe-OH, Fmoc-Leu-OH, Fmoc-Phe-OH, Fmoc-Arg(Pmc)-OH, Fmoc-Pro-OH, Fmoc-Arg(Pmc)-OH and Fmoc-Asn(Trt)-OH were arranged in the order of coupling. For the other lanes as well, these materials were arranged in the order of coupling. The gas used was gaseous nitrogen.

In cases where a peptide with fewer amino acids than on other lanes, that is a shorter fragment, is synthesized as on lanes F and G, no vials containing amino acid derivatives were placed and no reagents were supplied in accordance with the program of synthesis.

The patterns of reverse-phase HPLC of 8 different crude peptides obtained by simultaneous cleavage using the cleavage cocktail described above are shown in FIG. 6. The analytical conditions for the reversed-phase HPLC were as follows.

Column: SynProPep* RPC18 (4.6×250 mm)
*=Trademark
Eluent: 0.01N HCl/CH$_3$CN=85/15~55/45 (30 min.)
Flow Rate: 1.0 ml/min., Absorbance at 210 nm The results of FAB mass spectra at a main peak were also described here. All results show high purity and the results of mass spectra were calculated values.

Moreover, the primary structure of the peptides obtained here were confirmed by sequence analysis.

The peptides obtained here, namely obtained by simultaneous multiple syntheses, also show high homogeneity by sequence analysis.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A simultaneous multiple chemical synthesizer, comprising:

a plurality of reaction vessels wherein each vessel has a filter in the bottom portion thereof, whereon a solid-phase resin support is packed;

a plurality of needles, wherein each needle is connected to an aspirating line for injection of a reaction mixture into a respective reaction vessel, and to a gas supply line for each reaction vessel, and wherein each needle does not touch said resin when inserted in the respective reaction vessel;

one or more arms which are horizontally and vertically movable and hold said plurality of needles;

means for moving said one or more arms in a horizontal and vertical direction;

a bubbling gas line and a waste discharge line in connection with a respective reaction vessel, wherein each of said lines is connected to the bottom portion of its respective reaction vessel;

a plurality of purging means which move horizontally and vertically into said respective reaction vessels synchronously with the opening of said waste discharge lanes;

means for moving said purging means; and means for washing a portion of said needles and said purging means which come in contact with the reaction mixtures received in said reaction vessels.

2. The simultaneous multiple chemical synthesizer according to claim 1, wherein said purging means comprises a means for introducing gas to each reaction vessel so as to discharge the waste from the bottom portion of each reaction vessel to a bottle for waste liquid.

3. The simultaneous multiple chemical synthesizer according to claim 1, wherein said filter comprises a polyalkylene filter selected from the group consisting of polypropylene, polyethylene and polyvinylidene fluoride.

4. The simultaneous multiple chemical synthesizer according to claim 1, wherein said filter has a pore size of about 5 to 10 μm.

5. The simultaneous multiple chemical synthesizer according to claim 1, wherein more than one arm is horizontally and vertically movable and holds the respective needles.

6. The simultaneous multiple chemical synthesizer according to claim 1, wherein one arm is horizontally and vertically movable and holds the respective needles.

* * * * *